(12) United States Patent
Knowlton

(10) Patent No.: US 9,987,473 B2
(45) Date of Patent: *Jun. 5, 2018

(54) SKIN TREATMENT DEVICE AND METHODS

(71) Applicant: SRGI HOLDINGS, LLC, Henderson, NV (US)

(72) Inventor: Edward W. Knowlton, Henderson, NV (US)

(73) Assignee: SRGI HOLDINGS, LLC, Henderson, NV (US)

( * ) Notice: Subject to any disclaimer, the term of this patent is extended or adjusted under 35 U.S.C. 154(b) by 141 days.

This patent is subject to a terminal disclaimer.

(21) Appl. No.: 14/556,648

(22) Filed: Dec. 1, 2014

(65) Prior Publication Data

US 2015/0313622 A1  Nov. 5, 2015

Related U.S. Application Data

(63) Continuation of application No. 12/972,013, filed on Dec. 17, 2010, now Pat. No. 8,900,181.

(51) Int. Cl.
*A61M 35/00* (2006.01)
*A61B 17/3205* (2006.01)
(Continued)

(52) U.S. Cl.
CPC ......... *A61M 35/003* (2013.01); *A61B 17/322* (2013.01); *A61B 17/32053* (2013.01);
(Continued)

(58) Field of Classification Search
CPC ........... A61M 35/003; A61B 17/32053; A61B 17/32093; A61B 17/322;
(Continued)

(56) References Cited

U.S. PATENT DOCUMENTS 1,610,089 A * 12/1926 Heitler .................. A61F 15/006
602/42
3,867,942 A 2/1975 Bellantoni et al.
(Continued)

FOREIGN PATENT DOCUMENTS

| CN | 101530636 B | 2/2012 |
| KR | 20080100795 | 6/2008 |

(Continued)

OTHER PUBLICATIONS

Ito, Keita, Perren, Stephan M.; "Biology of Fracture Healing"; AO Principles of Fracture Management, AO Foundation Publishing, Jan. 2013, 5 pages.
(Continued)

*Primary Examiner* — Bradley J Osinski
(74) *Attorney, Agent, or Firm* — IPR Law Group, PC

(57) ABSTRACT

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

54 Claims, 10 Drawing Sheets

(51) Int. Cl.
*A61B 17/3209* (2006.01)
*A61B 17/322* (2006.01)
*A61M 5/46* (2006.01)
*A61B 17/32* (2006.01)
*A61B 17/00* (2006.01)

(52) U.S. Cl.
CPC ......... *A61B 17/32093* (2013.01); *A61M 5/46* (2013.01); *A61B 2017/00424* (2013.01); *A61B 2017/00747* (2013.01); *A61B 2017/00761* (2013.01); *A61B 2017/00792* (2013.01); *A61B 2017/3225* (2013.01); *A61B 2017/320064* (2013.01)

(58) Field of Classification Search
CPC .......... A61B 2017/00761; A61B 2017/00747; A61B 2017/320064; A61B 2017/3225
See application file for complete search history.

(56) References Cited

U.S. PATENT DOCUMENTS

| | | | |
|---|---|---|---|
| 4,018,228 A | 4/1977 | Goosen | |
| 4,098,278 A | 7/1978 | Schwartz | |
| 4,476,864 A | 10/1984 | Tezel | |
| 4,542,742 A | 9/1985 | Winkelman et al. | |
| 4,803,075 A | 2/1989 | Wallace et al. | |
| 5,123,907 A | 6/1992 | Romaine | |
| 5,141,513 A | 8/1992 | Fortune et al. | |
| 5,209,755 A | 5/1993 | Abrahan et al. | |
| 5,415,182 A | 5/1995 | Chin et al. | |
| 5,417,683 A | 5/1995 | Shiao | |
| 5,570,700 A | 11/1996 | Vogeler | |
| 5,643,308 A | 7/1997 | Markman | |
| 5,693,064 A | 12/1997 | Arnold | |
| 5,827,297 A | 10/1998 | Boudjema | |
| 5,858,019 A | 1/1999 | Ashraf | |
| 5,879,326 A | 3/1999 | Godshall et al. | |
| 5,922,000 A | 7/1999 | Chodorow | |
| 5,964,729 A | 10/1999 | Choi et al. | |
| 6,126,615 A | 10/2000 | Allen et al. | |
| 6,471,712 B2* | 10/2002 | Burres .................. | A45D 29/14 606/131 |
| 6,497,875 B1 | 12/2002 | Sorrell et al. | |
| 6,572,625 B1 | 6/2003 | Rassman | |
| 6,585,746 B2 | 7/2003 | Gildenberg | |
| 6,589,202 B1 | 7/2003 | Powell | |
| 6,626,865 B1 | 9/2003 | Prisell | |
| 6,669,685 B1 | 12/2003 | Rizoiu et al. | |
| 6,997,923 B2 | 2/2006 | Anderson et al. | |
| 7,204,828 B2 | 4/2007 | Rosiello | |
| 7,331,953 B2 | 2/2008 | Manstein et al. | |
| 7,354,423 B2 | 4/2008 | Zelickson et al. | |
| 7,621,933 B2 | 11/2009 | Bodduluri et al. | |
| 7,625,384 B2* | 12/2009 | Eriksson .............. | A61B 17/322 606/132 |
| 7,708,746 B2 | 5/2010 | Eriksson et al. | |
| 7,942,153 B2 | 5/2011 | Manstein et al. | |
| 7,962,192 B2 | 6/2011 | Bodduluri et al. | |
| 7,993,310 B2 | 8/2011 | Rosiello | |
| 8,535,299 B2 | 9/2013 | Giovannoli | |
| 8,540,731 B2* | 9/2013 | Kay ....................... | A61B 17/54 606/131 |
| 8,545,489 B2 | 10/2013 | Giovannoli | |
| 8,690,863 B2 | 4/2014 | Chan et al. | |
| 8,900,181 B2* | 12/2014 | Knowlton ............ | A61B 17/322 604/46 |
| 9,060,803 B2 | 6/2015 | Anderson et al. | |
| 9,351,792 B2 | 5/2016 | Manstein et al. | |
| 9,439,673 B2 | 9/2016 | Austen | |
| 9,468,459 B2 | 10/2016 | Hall et al. | |
| 2001/0053888 A1 | 12/2001 | Athanasiou et al. | |
| 2002/0052619 A1 | 5/2002 | Transue | |
| 2002/0088779 A1 | 7/2002 | Neev et al. | |
| 2002/0183688 A1 | 12/2002 | Lastovich et al. | |
| 2003/0036770 A1 | 2/2003 | Markman | |
| 2003/0069548 A1 | 4/2003 | Connelly et al. | |
| 2003/0216719 A1 | 11/2003 | Debenedictis et al. | |
| 2004/0082940 A1 | 4/2004 | Black et al. | |
| 2004/0087893 A1 | 5/2004 | Kwon | |
| 2004/0175690 A1 | 9/2004 | Mishra et al. | |
| 2005/0049582 A1 | 3/2005 | DeBenedictis et al. | |
| 2005/0283141 A1 | 12/2005 | Giovannoli | |
| 2006/0051404 A1 | 3/2006 | Yeshurun et al. | |
| 2006/0155266 A1 | 7/2006 | Manstein et al. | |
| 2007/0073217 A1 | 3/2007 | James | |
| 2007/0073327 A1 | 3/2007 | Giovannoli | |
| 2007/0179481 A1 | 8/2007 | Frangineas et al. | |
| 2007/0179516 A1* | 8/2007 | Mishra ................ | A61B 17/322 606/167 |
| 2007/0207131 A1 | 9/2007 | Boss et al. | |
| 2007/0224173 A1 | 9/2007 | Koullick et al. | |
| 2008/0172047 A1 | 7/2008 | Altshuler et al. | |
| 2010/0121307 A1 | 5/2010 | Lockard | |
| 2011/0009860 A1 | 1/2011 | Chomenky et al. | |
| 2011/0208089 A1 | 8/2011 | Sundheimer et al. | |
| 2011/0251602 A1 | 10/2011 | Anderson et al. | |
| 2011/0257588 A1 | 10/2011 | Knowlton | |
| 2011/0264115 A1 | 10/2011 | Asrani et al. | |
| 2011/0313429 A1 | 12/2011 | Anderson et al. | |
| 2012/0035599 A1 | 2/2012 | Sabir et al. | |
| 2012/0041430 A1 | 2/2012 | Anderson et al. | |
| 2012/0226214 A1 | 9/2012 | Gurtner et al. | |
| 2012/0271320 A1 | 10/2012 | Hall et al. | |
| 2012/0323139 A1 | 12/2012 | Richardson | |
| 2012/0323325 A1 | 12/2012 | Fulton | |
| 2013/0090669 A1 | 4/2013 | Bellomo | |
| 2013/0204273 A1 | 8/2013 | Sabir et al. | |
| 2013/0304090 A1 | 11/2013 | Oostman et al. | |
| 2014/0031801 A1 | 1/2014 | Giovannoli | |
| 2014/0303648 A1 | 10/2014 | Knowlton | |
| 2015/0216545 A1 | 8/2015 | Anderson et al. | |
| 2015/0238214 A1 | 8/2015 | Anderson et al. | |
| 2015/0366719 A1 | 12/2015 | Levinson et al. | |
| 2016/0095592 A1 | 4/2016 | Levinson et al. | |
| 2016/0192961 A1 | 7/2016 | Ginggen | |
| 2016/0310157 A1 | 10/2016 | Guiles et al. | |
| 2016/0310158 A1 | 10/2016 | Guiles et al. | |
| 2016/0310159 A1 | 10/2016 | Guiles et al. | |
| 2016/0317721 A1 | 11/2016 | Ginggen et al. | |
| 2016/0367280 A1 | 12/2016 | Austen | |
| 2017/0042561 A1 | 2/2017 | Hall et al. | |

FOREIGN PATENT DOCUMENTS

| | | |
|---|---|---|
| KR | 200303833 Y1 | 8/2013 |
| WO | 0145566 A1 | 6/2001 |
| WO | 2005072181 A2 | 8/2005 |
| WO | 2008002064 A1 | 1/2008 |
| WO | 2009146068 A1 | 12/2009 |
| WO | 2012103483 A2 | 8/2012 |
| WO | 2013013196 A1 | 1/2013 |
| WO | 2013013199 A2 | 1/2013 |
| WO | 2014028626 A1 | 2/2014 |
| WO | 2014089488 A2 | 6/2014 |

OTHER PUBLICATIONS

Ford, Charles N., Bless, Diane M; "Clinical Experience with Injectable Collagen for Vocal Fold Augmentation"; Larynscope 96(8), Aug. 1986, pp. 863-869.

Kaplan, Ernest N., Falces, Edward, Tolleth, Hale; "Clinical Utilization of Injectable Collagen"; From the Department of Surgery Division of Plastic and Reconstructive Surgery, Stanford University School of Medicine, Annals of Plastic Surgery, vol. 10, No. 6, Jun. 1983, 15 pages, Palo Alto, CA.

O'Connor, K.W., Lehman, G.A.; "Endoscopic Placement of Collagen at the Lower Esophageal Sphincter to Inhibit Gastroesophageal Reflux: a Pilot Study of 10 Medically Intractable Patients"; Gastrointestinal Endoscopy, Received Mar. 1987, Accepted May 1987, 7 pages, Indianapolis, IN.

(56) References Cited

OTHER PUBLICATIONS

Ford, Charles N., Staskowski, Paul A., Bless, Diane M.; "Autologous Collagen Vocal Fold Injection: A Preliminary Clinical Study"; Presented at the Meeting of the Middle Section of the American Laryngological, Rhinological and Otological Society Inc., Laryngoscope 105, Sep. 1995, 5 pages, Omaha NE.

Giordano, Antonio, Galderisi, Umberto, Marino, Ignazio R.; "From the Laboratory Bench to the Patient's Bedside: An Update on Clinical Trials with Mesenchymal Stem Cells"; Department of Experimental Medicine of Biotechnology and Molecular Biology, Second University of Naples, Oct. 2006, 10 pages, Naples Italy.

Matton, G., Anseeuw,A., De Keyser, F.; "The History of Injectable Biomaterials and the Biology of Collagen"; Aesthetic Plastic Surgery, vol. 9, Issue 2, Jun. 1985, 8 pages, Gent Belguim.

Klein, Arnold William; "Implantation Technics for Injectable Collagen"; Journal of the American Academy of Dermatology, vol. 9, Issue 2, Aug. 1983, pp. 224-228. Beverly Hills, CA.

Cooperman, Linda, S., Mackinnon, Victoria, Bechler, Gail, Pharriss, Bruce B.; "Injectable Collagen: A Six-Year Clinical Investigation"; Aesthetic Plastic Surgery, vol. 9, Issue 2, Jun. 1985, pp. 145-151.

Ford, Charles N., Bless, Diane M.; "A Preliminary Study of Injectable Collagen in Human Vocal Fold Augmentation"; From the Division of Otolaryngology, Department of Surgery, University of Wisconsin and Middleton Veterans Administration Hospital and Department of Communicative Disorders, University of Wisconsin and Waisman enter on Mental Retardation and Human Development; Presented at the Annual Meeting of the American Academy of Otolaryngology—Head and Neck Surgery, Sep. 1985, 9 pages, Las Vega, NV.

Ford, Charles N., Bless, Diane M., Loftus, Jean M.; "Role of Injectable Collagen in the Treatment of Glottic Insufficiency: A Study of 119 Patients"; Annals of Otology, Rhinology and Laryngology, vol. 101, Issue 3, Mar. 1992, 11 pages, Madison WI.

Frey, P., Berger, D., Jenny, P., Herzog, B.; " Subureteral Collagen Injection for the Endoscopic Treatment of Vesicoureteral Reflux in Children. Followup Study of 97 Treated Ureters and Histological Analysis of Collagen Implants"; Department of Pediatric Surgery, CHUV, Lausanne and University Children's Hospital; The Journal of Urology, vol. 148 pp. 718-723, Aug. 1992, Basel Switzerland.

Shortliffe, Linda M. Dairiki, Freiha, Fuad S., Kessler, Robert, Stamely,Thomas A., Constantinou, Christos E.: "Treatment of Urinary Incontinence by the Periurethral Implantation of Glutaraldehyde Cross-Linked Collagen"; The Journal of Urology, vol. 141, Mar. 1989, 3 pages, Palo Alto, CA.

International Search Report and Written Opinion for International PCT Application No. PCT/US2013/073678 dated May 27, 2014, 18 pages.

International Search Report and Written Opinion for International PCT Application No. PCT/US2014/058886 dated Mar. 3, 2015, 22 pages.

International Search Report and Written Opinion for International PCT Application No. PCT/US2015/047695 dated Jan. 28, 2016, 40 pages.

International Search Report and Written Opinion for International PCT Application No. PCT/US2015/047721 dated Feb. 3, 2016, 20 pages.

International Search Report and Written Opinion for International PCT Application No. PCT/US2016/016834 dated May 17, 2016, 11 pages.

Supplementary European Search Report for EP Application No. EP13859972 dated Jun. 10, 2016, 6 pages.

Alguire, Patrick; Mathes, Barbara M.; "Skin Biopsy Techniques for the Internist"; received from the Division of Internal Medicine (PCA) and the Division of Dermatology (BMM), University of Florida, Gainesville, vol. 13, Jan. 1998, 9 pages.

Zuber, Thomas J.; "Fusiform Exision"; American Family Physician, vol. 67, No. 7, Apr. 2003, 6 pages.

Russe, Elisabeth, et al. "Micro-Fractional, Direction Skin Tightening: A Porcine Model"; Lasers in Surgery and Medicine 48:264-269, Accepted Nov. 4, 2015, Published online Dec. 2, 2015 in Wiley Online Library (wileyonlinelibrary.com), 6 pages.

\* cited by examiner

SKIN TREATMENT DEVICE AND METHODS

RELATED APPLICATIONS

This application is a continuation of U.S. patent application Ser. No. 12/972,013, filed Dec. 17, 2010, now U.S. Pat. No. 8,900,181, which claims priority to U.S. Provisional Patent Application No. 61/281,141, filed Dec. 18, 2009, and entitled "Razor/Razor Blade Toolbox of Disposable Plastic Surgical Instruments," by Edward W. Knowlton, and is hereby incorporated herein by reference.

BACKGROUND

The aging process is most visibly depicted by the development of dependent skin laxity. This life long process may become evident as early as the third decade of life and will progressively worsen over subsequent decades. Histological research has shown that dependant stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas is the head and neck. In this region, prominent "turkey gobbler" laxity of neck and "jowls" of the lower face are due to an unaesthetic dependency of skin in these areas. The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Some of the inherent adverse features of these surgical procedures are post-operative pain, scarring and the risk of surgical complications. Even though the aesthetic enhancement of these procedures is an acceptable tradeoff to the significant surgical incisions required, permanent and extensive scarring is always an incumbent part of these procedures. For this reason, Plastic Surgeons design these procedures to hide the extensive scarring around anatomical borders such as the hairline (Facelift), the inframmary fold (Mastopexy) and the inguinal crease (Abdominoplasty). However, other skin laxity regions such as the Suprapatellar (upper-front) knee are not amendable to Plastic Surgical resections due to the poor tradeoff with a more visible surgical scar. Recently, electromagnetic medical devices that create a reverse thermal gradient (i.e., Thermage) have attempted with variable success to tighten skin without surgery. At this time, these electromagnetic devices are best deployed in patients with a moderate amount of skin laxity due to the limitations of electromagnetic devices and potential side effects of surgery.

The foregoing examples of the related art and limitations related therewith are intended to be illustrative and not exclusive. Other limitations of the related art will become apparent upon a reading of the specification and a study of the drawings.

DETAILED DESCRIPTION OF EMBODIMENTS

Figure 1A:
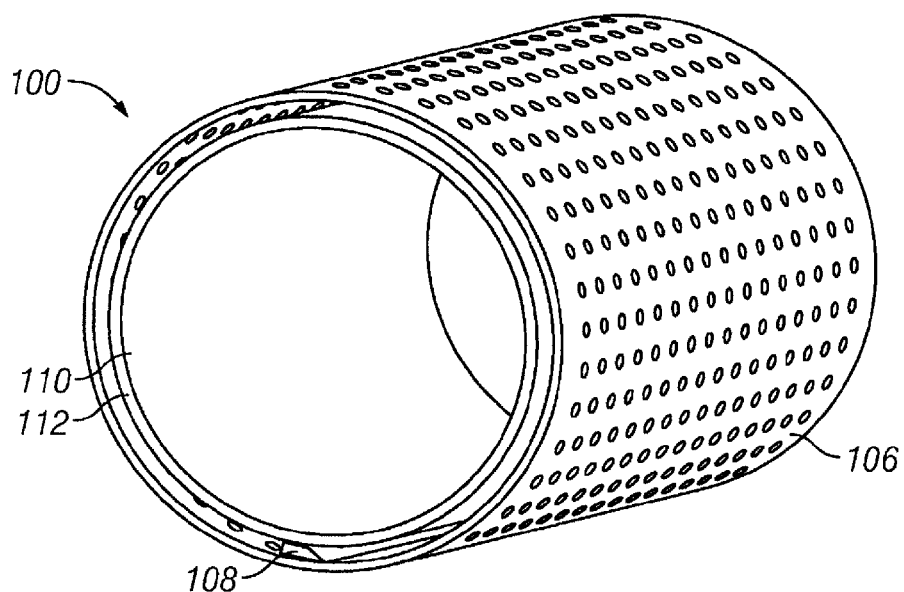
FIGS. 1(a)-(c) depict examples of a full rolling/rotating pixel drum/cylinder applicable to a skin surface for tightening.

The approach is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast), the minimally invasive surgical approach performs pixilated transection/resection of excess skin, replacing Plastic Surgery with its incumbent scarring. Typically, the procedure will be performed in an office setting under a local anesthetic with minimal perioperative discomfort. In comparison to a prolonged healing phase from plastic surgery, only a short recovery period will be required and the only recovery requirement will be the need to wear a support garment over the treatment area for 5 days. There will be little or no pain associated with the procedure. The small (½ mm to 1 mm) intradermal circular skin defects will be closed with the application of an adherent Flexan (3M) sheet. Functioning as a large butterfly bandage, the Flexan sheet can be pulled in a direction ("vector") that maximizes the aesthetic contouring of the treatment area. A compressive elastic garment will be applied over the dressing to further assist aesthetic contouring. After completion of the initial healing phase, the multiplicity of small linear scars within the treatment area will not be visibly apparent. It is also predicted that additional skin tightening will occur subsequently over several months due to the delayed wound healing response. Other potential applications include the treatment of Snoring/Sleep apnea, Orthopedics/Physiatry, Vaginal Tightening and tightening of gastrointestinal sphincters. During recovery, the treatment area is covered with a Flexan dressing and a compressive garment that promotes the wound healing process in the most effective direction.

Device for Skin Treatment

Figure 1B:
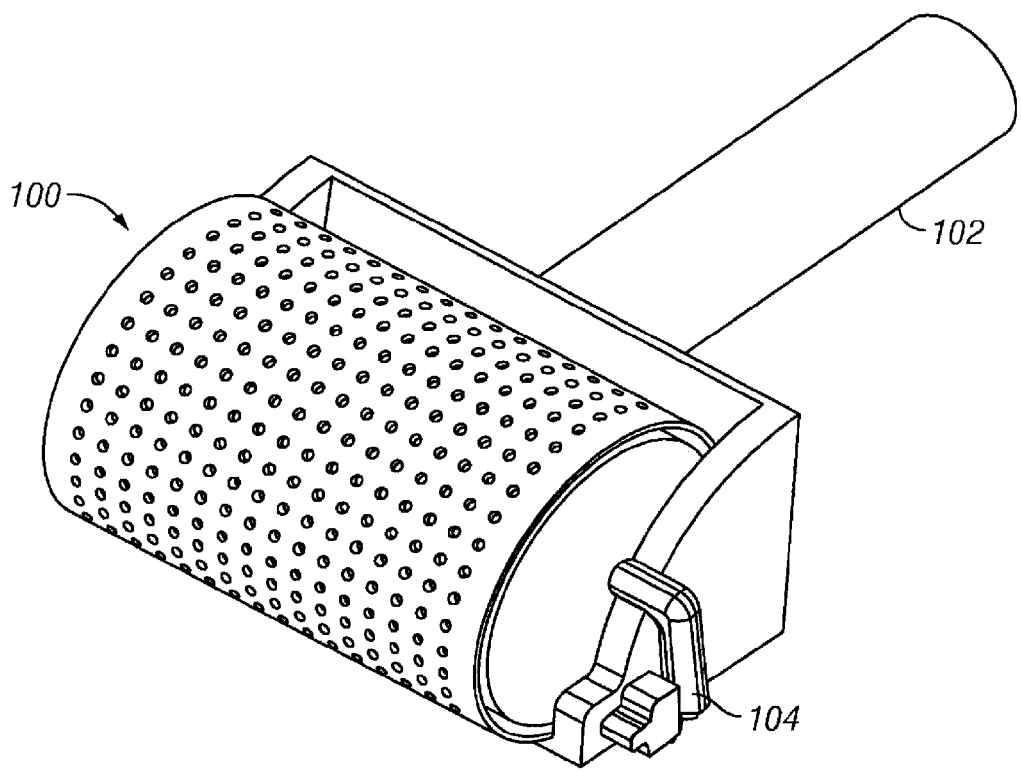
Figure 1C:
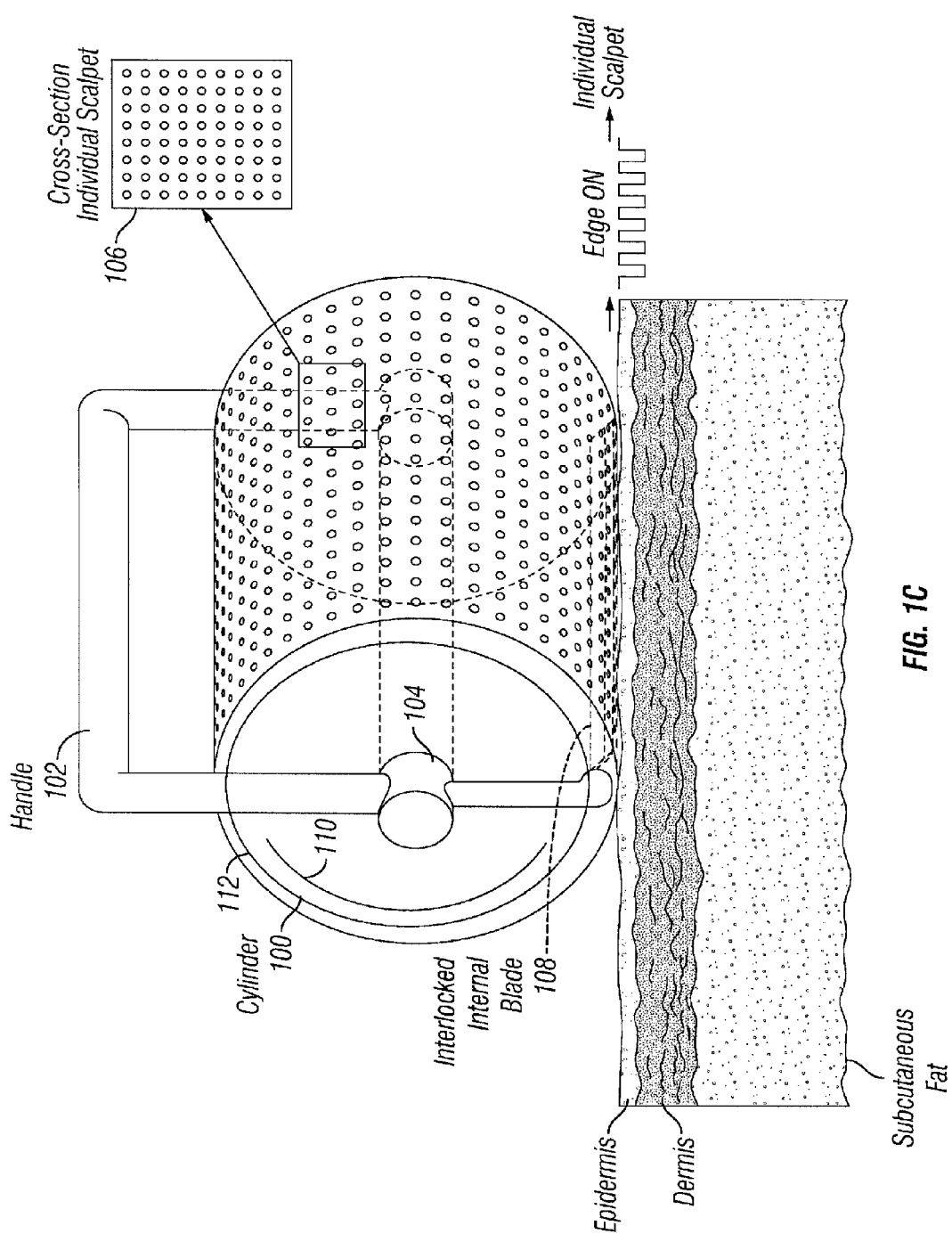

FIGS. 1(a)-(c) depict examples of a full rolling/rotating pixel drum/cylinder 100 applicable to the skin surface for tightening. Although the diagrams depict components as functionally separate, such depiction is merely for illustrative purposes. It will be apparent that the components portrayed in this figure can be arbitrarily combined or divided into separate hardware components.

Referring now to FIGS. 1(a)-(c), FIG. 1(a) depicts an example of rolling pixel drum 100, FIG. 1(b) depicts an example of a rolling pixel drum 100 assembled on a handle, and FIG. 1(c) depicts an example of a rolling pixel drum 100 being applied to the skin surface for tightening. FIGS. 2(a)-(d) further depict examples of dissected internal structure of a half drum depicted in FIGS. 1(a)-(d).

As with other pixel devices, the geometry of the pixel drum 100 can be a variety of shapes without limitation i.e., circular, semicircular, elliptical, square, flat, or rectangular. In some embodiments, the pixel drum 100 is supported by an axel/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., ½ mm to 1 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axel/handle assembly 102 and/or connected to outriggers attached to the central axel assembly 102. In some alternative embodiments, the internal blade 108 is not connected to the drum axel assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin can be transected. It is predicted that up to 50% of the skin's surface area can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In some embodiments, the blade 108 is placed external to the drum 100 and the scalpet array 106 where the base of the incised circular skin plugs is transected. In some embodiments, the external blade 108 is connected to the drum axel assembly 102 when the base of the incisions of skin is transected. In some alternative embodiments, the external blade 108 is not connected to the drum axel assembly 102 when the base of the incisions of skin is transected. The adherent membrane 110 that extracts and aligns the transected skin segments onto the membrane 110, which is later placed over a skin defect site of a patient. In some embodiments, blade 108 (either internal or external) can be a fenestrated layer of blade aligned to the scalpet array 106.

Figure 2A:
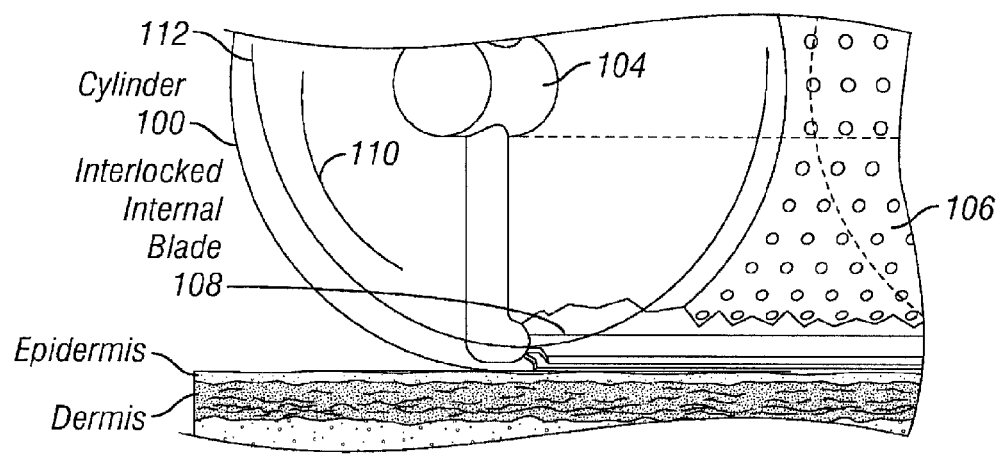
FIGS. 2(a)-(d) depict examples of dissected internal structure of a half drum depicted in FIGS. 1(a)-(d).
Figure 2B:
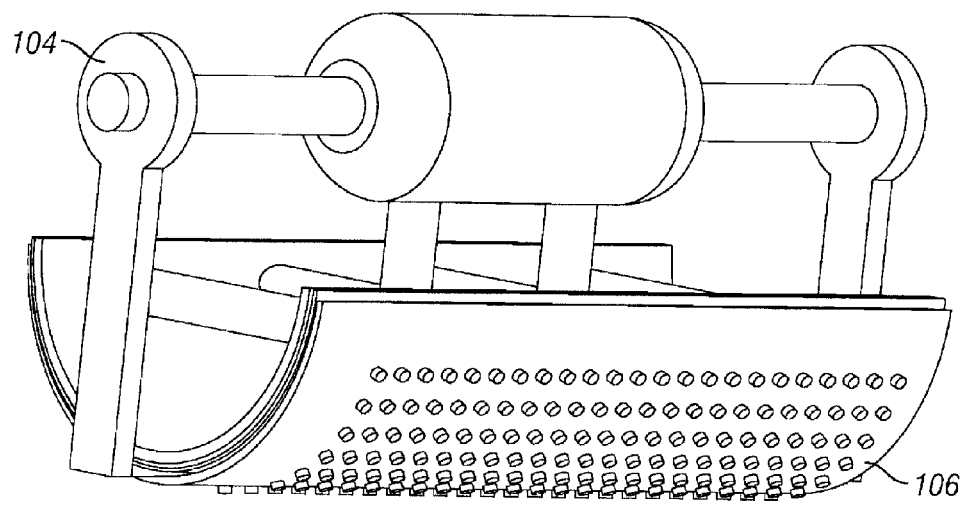
Figure 2C:
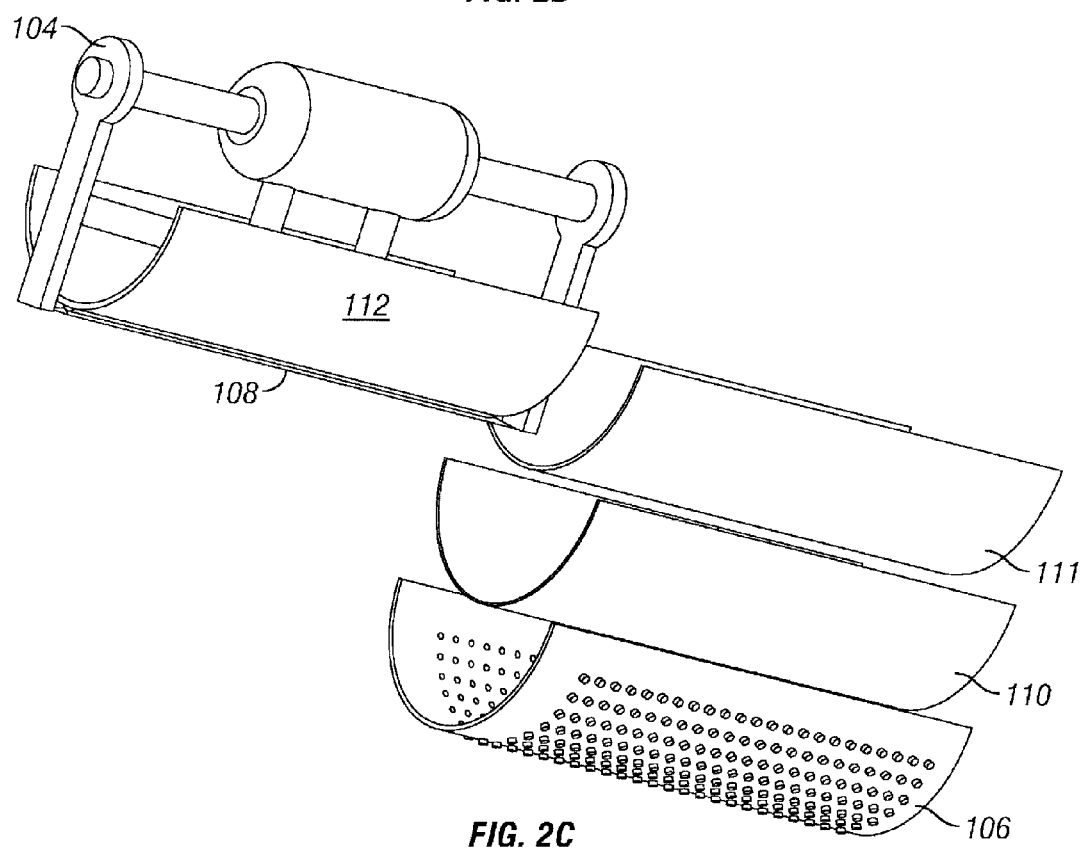
Figure 2D:
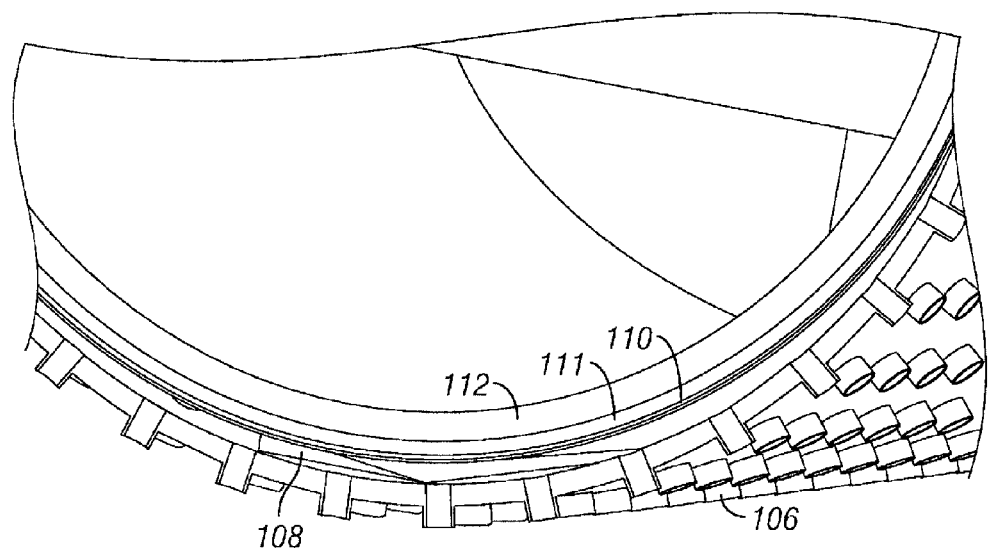

In some embodiments, the conformable adherent membrane 110 can be semi-porous to allow for drainage at a recipient skin defect when the membrane with the aligned transected skin segments is extracted from the drum and applied as a skin graft. In some embodiments, the adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. In some embodiments, the adherent semi-porous drum membrane 110 can also be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100 as shown in FIGS. 2(c)-(d).

In some embodiments, the internal drum harvester 112 of the pixel drum 110 is disposable and replaceable. Limit and/or control the use of the disposable components can be accomplished by means that includes but is not limited to electronic, eprom, mechanical, durability. The electronic and/or mechanical records and/or limits of number of drum rotations for the disposable drum as well as the time of use for the disposable drum can be recorded, controlled and/or limited either electronically or mechanically.

Figure 3A:
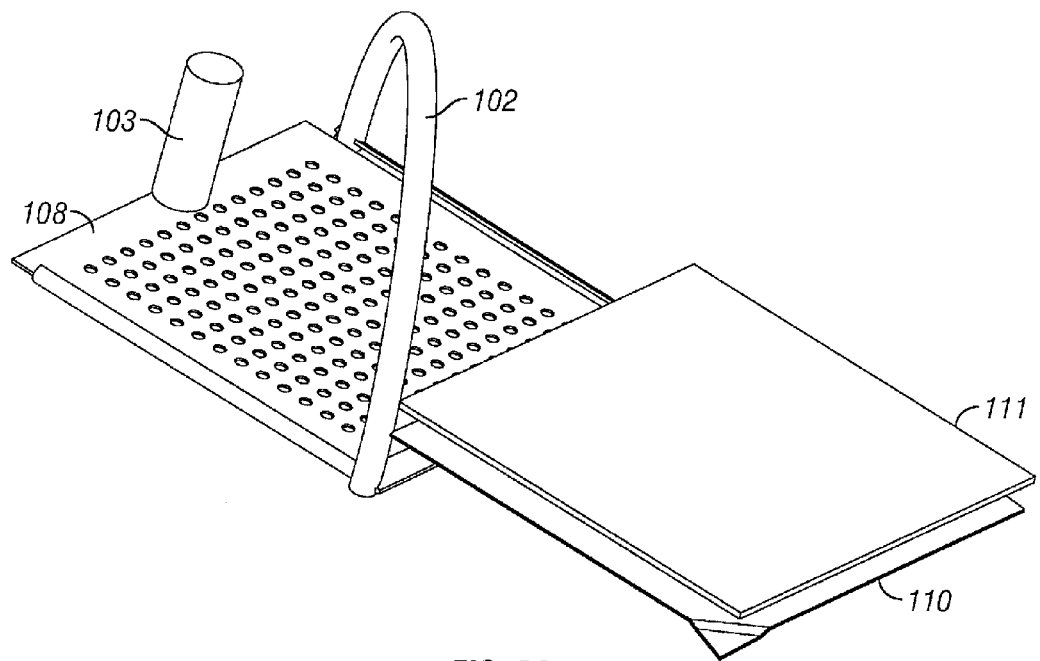
FIGS. 3(a)-(d) depict examples of an oscillating flat array of scalpets and blade either powered electrically or deployed manually (unpowered).
Figure 3B:
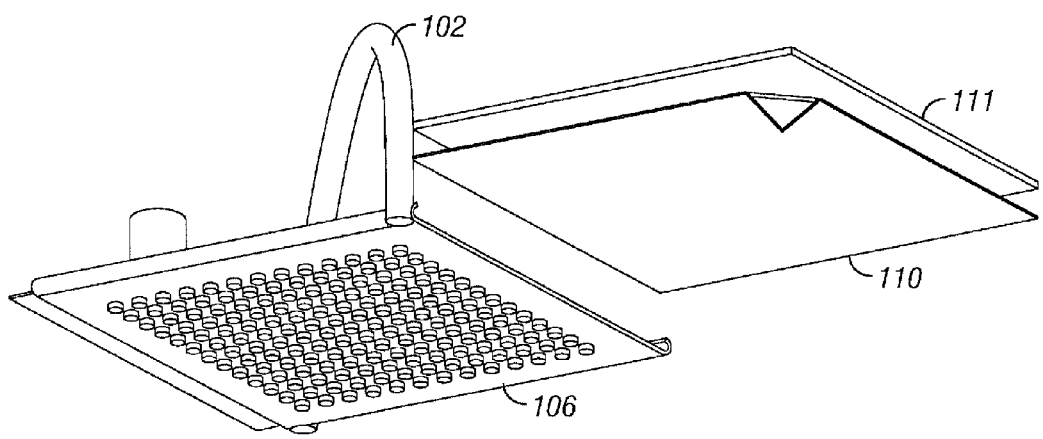
Figure 3C:
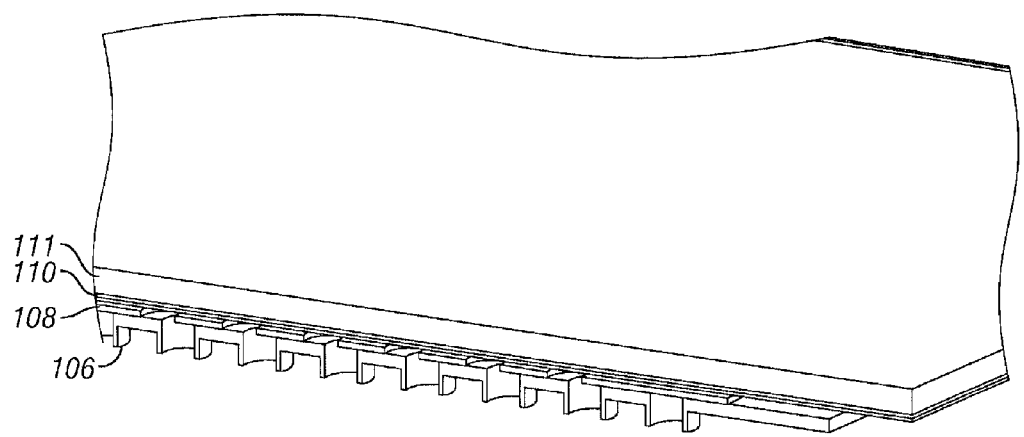
Figure 3D:
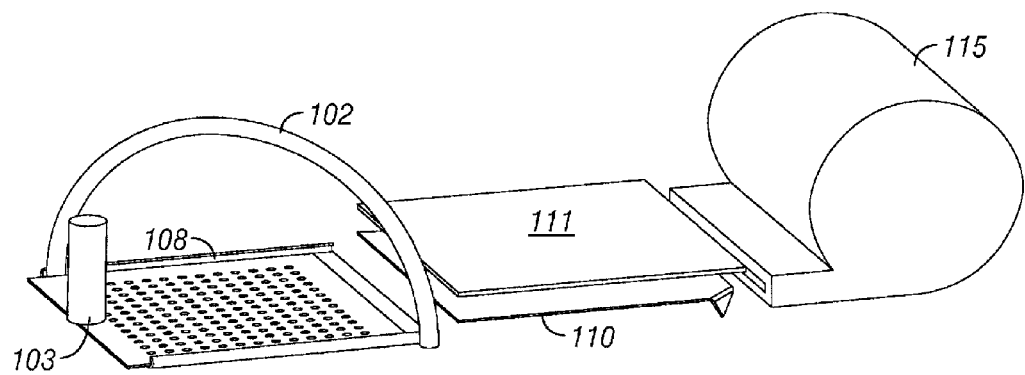

In some embodiments, an oscillating flat array of scalpets and blade as shown in FIGS. 3(a)-(d) either powered electrically or deployed manually (unpowered) can be used for skin tightening as alternative to the drum/cylinder depicted in FIGS. 1(a)-(c) and 2(a)-(d). Here, blade 108 can be a fenestrated layer of blade aligned to the scalpet array 106. FIGS. 3(a)-(b) depict top and bottom views of the flat array where the instrument handle 102 is separated from the blade handle 103 and the adherent membrane 110 can be peeled away from the adhesive backer 111. FIG. 3(c) depict a close-up view of the flat array when the array of scalpets 106, blades 108, adherent membrane 110 and the adhesive backer 111 are assembled together. As assembled, the flat array of scalpets can be metered to provide a uniform harvest or a uniform resection. In some embodiments, the flat array of scalpets may further include a feeder component 115 for the adherent harvesting membrane 110 and adhesive backer 111 as shown in FIG. 3(d).

Figure 4:
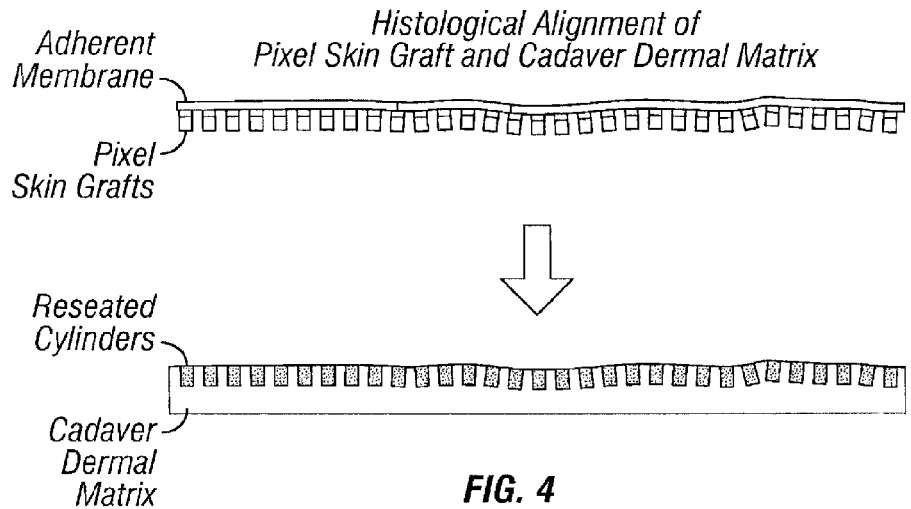
FIG. 4 depicts an example of a cadaver dermal matrix cylindrical transected similar in size to the harvested skin pixel grafts to provide histological alignment of the pixilated graft into the cadaver dermal framework.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In some embodiments, the cadaver dermal matrix can also be cylindrical transected similar in size to the harvested skin pixel grafts to provide histological alignment of the pixilated graft into the cadaver dermal framework as shown in FIG. 4. In some embodiments, the percentage of harvest of the donor site can be determined in part by the induction of a normal dermal histology at the skin defect site of the recipient as shown in FIG. 4, i.e., a normal (smoother) surface topology of the skin graft is facilitated. With either the adherent membrane or the dermal matrix embodiment, major advantage of the pixel drum harvester includes the ability to harvest a large surface area for grafting with visible scarring of the patient's donor site significantly reduced or eliminated.

In some embodiments, the pixel drum 100 may evoke cellular and/or extracellular responses that are obligatory to the clinical outcomes achieved and a physical reduction of the skin surface area may occur due to the transected/pixilated skin, i.e., creation of the skin plugs. In addition, a subsequent tightening of the skin is predicted due to the delayed wound healing response. Each skin pixilation may initiate the obligate wound healing sequence in multiple phases:

- The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.
- The second phase (of Fibroplasia) commences within 4-5 days of "wounding". During this phase, there is migration and mitotic multiplication of fibroblasts. Fibroplasia of the wound has two key features: the deposition of neocollagen and the myofibroblastic contraction of the wound. Histologically, the deposition of neocollagen can be identified microscopically as compaction and thickening of the dermis. Although this is a static process, the tensile strength of the wound significantly increases. The other feature of Fibroplasia is a dynamic physical process that results in a three dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia will be dermal contraction along with the deposition of a static supporting scaffolding of neocollagen with a tightened framework. The clinical effect can be seen as a delayed tightening of skin with smoothing of skin texture over several months. The clinical endpoint is a more youthful appearing skin envelope of the treatment area.
- A third and final phase of the delayed wound healing response is maturation. During this phase there is a strengthening and remodeling of the treatment area due to an increased cross-linkage of the collagen fibril matrix (of the dermis). This final stage commences with 6 to 12 months after "wounding" and may extend for at least 1-2 years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel drum 100 described above may have additional medically related applications. In some embodiments, the pixel drum 100 can transect a variable portion of any soft tissue structure without resorting to a standard surgical resection. More specifically, the reduction of an actinic damaged area of skin via the pixel drum 100 should reduce the incidence of skin cancer. For the treatment of sleep apnea and snoring, a pixilated mucosal reduction (soft palate, base of the tongue and lateral pharyngeal walls) via the pixel drum 100 would reduce the significant morbidity associated with more standard surgical procedures. For birth injuries of the vaginal vault, pixilated skin and vaginal mucosal resection via the pixel drum 100 would reestablish normal pre-partum geometry and function without resorting to an A&P resection. Related female stress incontinence could also be corrected in a similar fashion.

Drug Delivery Device

For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 5:
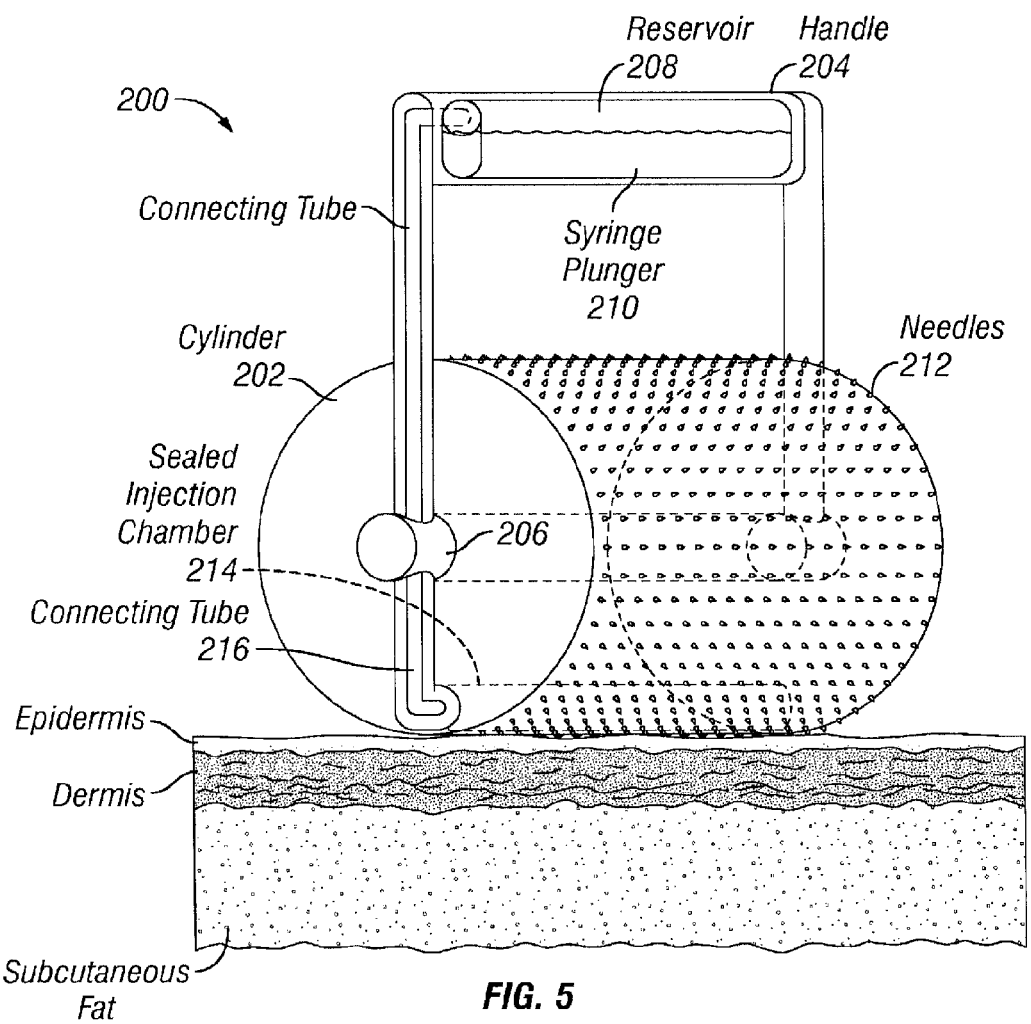
FIG. 5 depicts example of a drum-based drug delivery device being applied to the skin surface for drug injection.

The drug delivery device 200 depicted in FIG. 5 successfully addresses the limitations and drawbacks of other drug delivery systems. A drum/cylinder 202 depicted in FIG. 5 is supported by an axel/handle assembly 204 and rotated around a drum rotation component 206. The handle assembly 204 may further include a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 6A:
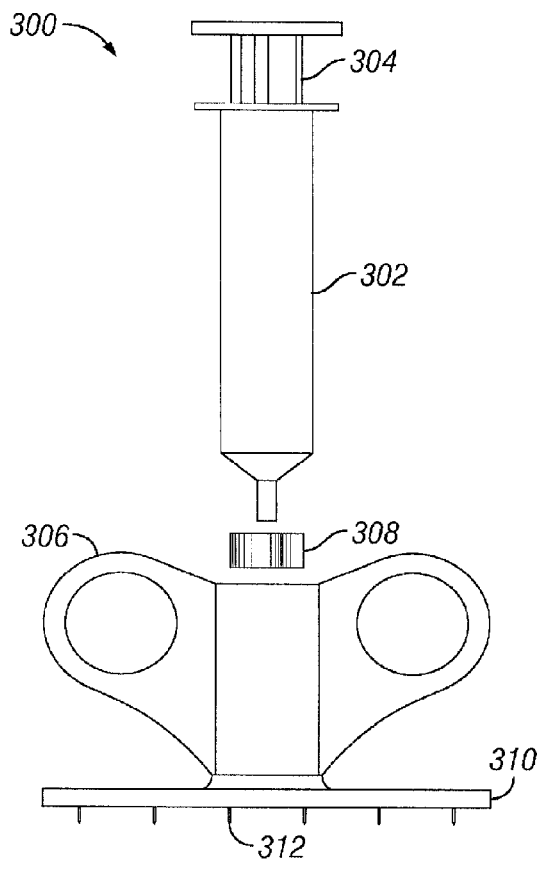
FIG. 6(a)-(c) depict examples of a drug delivery device based on flat array of needles being applied to the skin surface for drug injection.
Figure 6B:
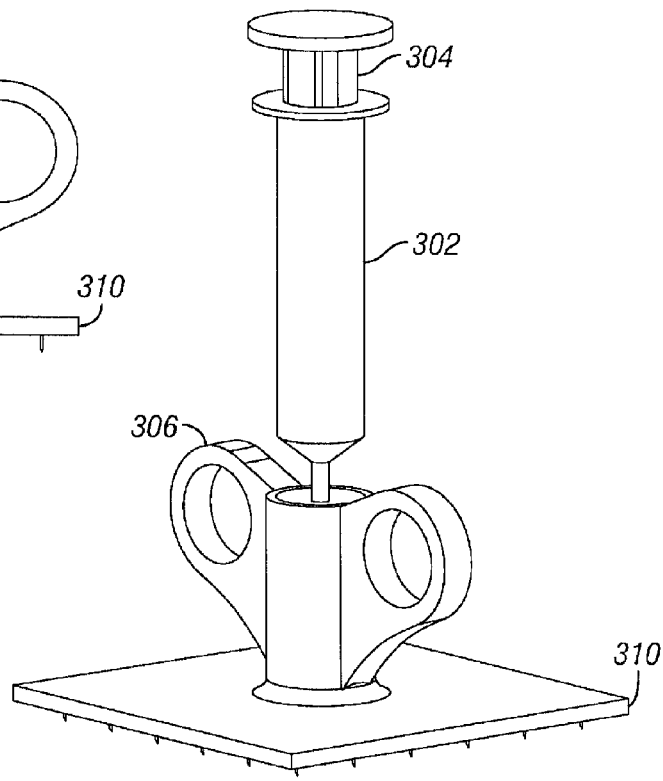
Figure 6C:
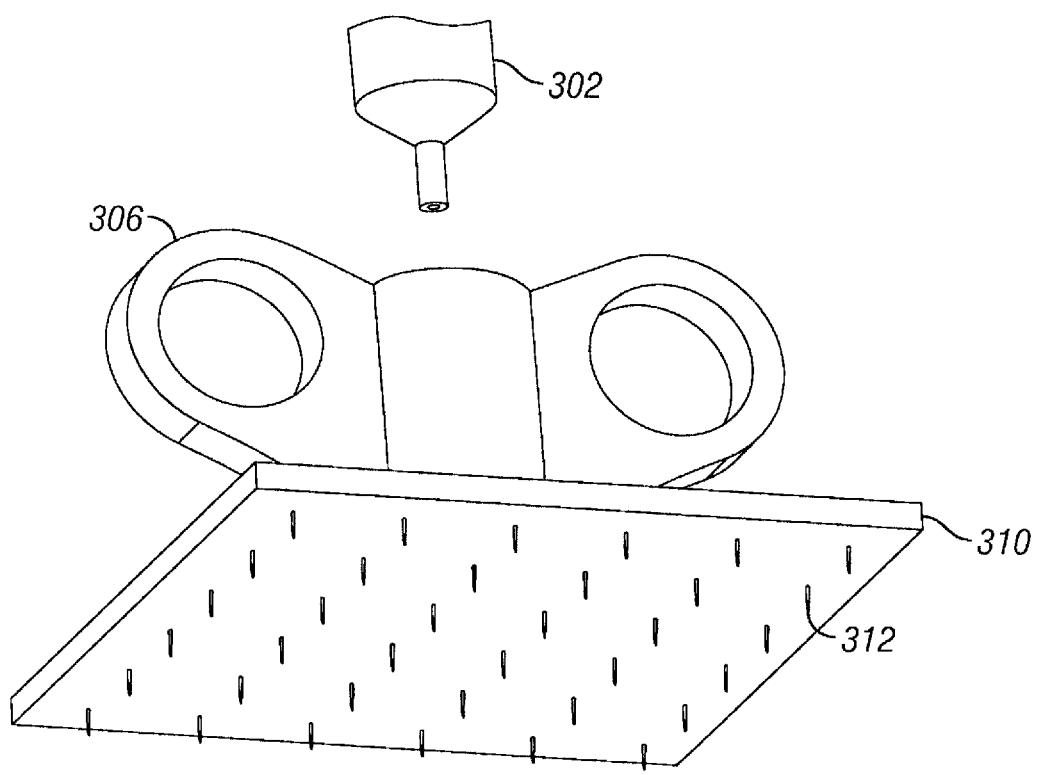

FIGS. 6(a)-(c) depict alternative embodiments of a drug delivery device 300, where a flat array of fine needles 312 of uniform length positioned on manifold 310 can be utilized for drug delivery. In the examples of FIG. 6(a), syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin. FIGS. 6(*b*)-(*c*) depict top and bottom views of the drug delivery device 300 with a flat array of fine needles 312, respectively.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

The foregoing description of various embodiments of the invention has been presented for purposes of illustration and description. Various methods of the invention are applicable to variety of medical, dermatological and surgical methods including reconstructive and plastic surgery procedures and minimally invasive procedures. It is not intended to limit the invention to the precise forms disclosed. Many modifications, variations and different combinations of embodiments will be apparent to practitioners skilled in this art. Further, elements from one embodiment can be readily recombined with one or more elements from other embodiments.

What is claimed is:

1. A system, comprising:
   a carrier configured to include a scalpet assembly;
   the scalpet assembly comprising a scalpet array coupled to a substrate, wherein the scalpet array includes a plurality of scalpets, wherein the substrate is configured to maintain a configuration of the plurality of scalpets, wherein the scalpet array is configured to be deployed to a target site and to generate a plurality of incised skin pixels at a target site; and
   a capture system configured to capture and remove the plurality of incised skin pixels from the target site, wherein the capture system includes an adherent substrate configured to capture the plurality of incised skin pixels.

2. The system of claim 1, wherein at least one scalpet of the scalpet array comprises a cylindrical scalpet with a circular cross-section, wherein a distal end of the at least one scalpet is configured to generate circular incisions at the target site.

3. The system of claim 2, wherein the distal end of the at least one scalpet includes a sharpened edge.

4. The system of claim 2, wherein an interior region of the at least one scalpet includes a hollow region.

5. The system of claim 1, comprising a vibration system coupled to the scalpet array.

6. The system of claim 5, wherein the vibration system is configured to couple oscillatory force to the scalpet array.

7. The system of claim 1, wherein the adherent substrate comprises at least one of a flexible substrate and a semi-porous membrane.

8. The system of claim 1, wherein the capture system includes a vacuum system configured to evacuate tissue including the plurality of incised skin pixels from the target site.

9. The system of claim 1, wherein the target site includes a donor site, wherein the plurality of incised skin pixels is harvested at the donor site.

10. The system of claim 9, wherein the plurality of incised skin pixels generate a plurality of skin defects at the donor site.

11. The system of claim 10, wherein the plurality of skin defects have a diameter approximately in a range of 0.5 millimeters (mm) to 1.0 mm.

12. The system of claim 9, wherein the target site includes a recipient site, wherein the scalpet array is configured to be deployed to the recipient site to generate a plurality of skin defects at the recipient site.

13. The system of claim 12, wherein the scalpet array is configured to generate the plurality of skin defects at the recipient site by generating and removing a second plurality of incised skin pixels.

14. The system of claim 12, wherein the plurality of skin defects at the recipient site configure the recipient site to receive a skin graft comprising the plurality of incised skin pixels from the target site.

15. The system of claim 12, wherein the plurality of skin defects at the recipient site is configured to evoke neovascularization in the plurality of incised skin pixels inserted at the recipient site.

16. The system of claim 12, wherein the plurality of skin defects at the recipient site is configured to evoke a wound healing response in the plurality of incised skin pixels inserted at the recipient site.

17. The system of claim 12, comprising an adherent substrate configured to capture the plurality of incised skin pixels at the donor site and transfer the plurality of incised skin pixels to the recipient site.

18. The system of claim 17, wherein the adherent substrate is configured to maintain relative positioning of the plurality of incised skin pixels during transfer to and application at the recipient site.

19. The system of claim 17, wherein the adherent substrate is configured to apply the plurality of incised skin pixels to the skin defects at the recipient site.

20. The system of claim 17, wherein the adherent substrate is configured to align the plurality of incised skin pixels with the skin defects at the recipient site.

21. The system of claim 12, comprising at least one bandage configured for application at the target site, wherein the at least one bandage is configured to apply force to close the target site.

22. The system of claim 21, wherein the force is a directional force configured to control a direction of the closure at the target site.

23. The system of claim 1, comprising a cutting member configured to transect the plurality of incised skin pixels.

24. The system of claim 23, wherein the cutting member includes a blade aligned to the scalpet array.

25. A method comprising:
   aligning a scalpet array of a device at a donor site, wherein the scalpet array comprises a plurality of scalpets arranged in a configuration;
   incising a plurality of skin pixels at the donor site by applying a load to the scalpet array, wherein the plurality of skin pixels corresponds to the plurality of scalpets;

capturing the plurality of incised skin pixels and removing the plurality of incised skin pixels from the donor site, wherein the capturing comprises capturing the plurality of incised skin pixels on an adherent substrate.

26. The method of claim 25, wherein the capturing comprises capturing the plurality of incised skin pixels and transferring them to a recipient site while maintaining the configuration.

27. The method of claim 25, wherein the adherent substrate comprises at least one of a flexible substrate and a semi-porous membrane.

28. The method of claim 25, wherein the capturing comprises capturing the plurality of incised skin pixels using a vacuum system configured to evacuate tissue from the target site.

29. The method of claim 25, comprising transecting bases of the plurality of incised skin pixels.

30. The method of claim 25, comprising applying a bandage to the donor site following the incising of the plurality of skin pixels, wherein the bandage closes the donor site and controls a direction that a plurality of skin defects corresponding to the plurality of incised skin pixels are closed.

31. The method of claim 25, comprising generating a plurality of skin defects at a recipient site with the scalpet array.

32. The method of claim 31, comprising applying the plurality of incised skin pixels to the plurality of skin defects at the recipient site.

33. The method of claim 32, wherein the generating of the plurality of skin defects at the recipient site comprises generating the skin defects with a same configuration as the plurality of incised skin pixels of the donor site.

34. The method of claim 32, wherein the capturing comprises aligning the plurality of incised skin pixels on an adherent substrate.

35. The method of claim 34, wherein the applying of the plurality of incised skin pixels comprises applying the plurality of incised skin pixels from the adherent substrate directly to the plurality of skin defects at the recipient site.

36. The method of claim 35, wherein the applying of the plurality of incised skin pixels comprises aligning the plurality of incised skin pixels with the plurality of skin defects at the donor site.

37. The method of claim 36, wherein the applying of the plurality of incised skin pixels at the recipient site comprises inserting the plurality of incised skin pixels into corresponding skin defects at the recipient site.

38. The method of claim 32, comprising applying a bandage to the recipient site following the applying of the plurality of incised skin pixels at the recipient site, wherein the bandage generates a force at the recipient site.

39. The method of claim 38, wherein the bandage comprises an adherent membrane.

40. The method of claim 39, wherein the bandage is configured to transfer the plurality of incised skin pixels from the donor site.

41. The method of claim 39, wherein the bandage is configured to promote neovascularization of the plurality of incised skin pixels inserted at the recipient site.

42. The method of claim 39, wherein the bandage is configured to promote alignment of the plurality of incised skin pixels inserted at the recipient site.

43. A method comprising:
aligning a scalpet array of a device at a donor site, wherein the scalpet array comprises a plurality of scalpets arranged in a configuration;
incising a plurality of skin pixels at the donor site by applying a load to the scalpet array, wherein the plurality of skin pixels corresponds to the plurality of scalpets;
capturing the plurality of incised skin pixels and removing the plurality of incised skin pixels from the donor site;
generating a plurality of skin defects at a recipient site with the scalpet array.

44. The method of claim 43, comprising applying the plurality of incised skin pixels to the plurality of skin defects at the recipient site.

45. The method of claim 44, wherein the generating of the plurality of skin defects at the recipient site comprises generating the skin defects with a same configuration as the plurality of incised skin pixels of the donor site.

46. The method of claim 44, wherein the capturing comprises aligning the plurality of incised skin pixels on an adherent substrate.

47. The method of claim 46, wherein the applying of the plurality of incised skin pixels comprises applying the plurality of incised skin pixels from the adherent substrate directly to the plurality of skin defects at the recipient site.

48. The method of claim 47, wherein the applying of the plurality of incised skin pixels comprises aligning the plurality of incised skin pixels with the plurality of skin defects at the donor site.

49. The method of claim 48, wherein the applying of the plurality of incised skin pixels at the recipient site comprises inserting the plurality of incised skin pixels into corresponding skin defects at the recipient site.

50. The method of claim 44, comprising applying a bandage to the recipient site following the applying of the plurality of incised skin pixels at the recipient site, wherein the bandage generates a force at the recipient site.

51. The method of claim 50, wherein the bandage comprises an adherent membrane.

52. The method of claim 51, wherein the bandage is configured to transfer the plurality of incised skin pixels from the donor site.

53. The method of claim 51, wherein the bandage is configured to promote neovascularization of the plurality of incised skin pixels inserted at the recipient site.

54. The method of claim 51, wherein the bandage is configured to promote alignment of the plurality of incised skin pixels inserted at the recipient site.

* * * * *